（12) United States Patent
Driscoll

(10) Patent No.: US 10,306,899 B2
(45) Date of Patent: Jun. 4, 2019

(54) BEEF CUTTING METHOD AND SYSTEM

(71) Applicant: JARVIS PRODUCTS CORPORATION, Middletown, CT (US)

(72) Inventor: Daniel Driscoll, Middletown, CT (US)

(73) Assignee: JARVIS PRODUCTS CORPORATION, Middletown, CT (US)

(*) Notice: Subject to any disclaimer, the term of this patent is extended or adjusted under 35 U.S.C. 154(b) by 0 days.

(21) Appl. No.: 16/174,882

(22) Filed: Oct. 30, 2018

(65) Prior Publication Data

US 2019/0069563 A1    Mar. 7, 2019

Related U.S. Application Data

(63) Continuation of application No. 15/886,323, filed on Feb. 1, 2018, now Pat. No. 10,117,438, which is a continuation-in-part of application No. 15/663,097, filed on Jul. 28, 2017, now Pat. No. 9,955,702.

(60) Provisional application No. 62/414,240, filed on Oct. 28, 2016, provisional application No. 62/520,143, filed on Jun. 15, 2017.

(51) Int. Cl.
    A22B 5/00     (2006.01)
    A22B 5/20     (2006.01)
    G01N 33/12    (2006.01)
    A22C 17/02    (2006.01)

(52) U.S. Cl.
    CPC ............ A22B 5/0041 (2013.01); A22B 5/007 (2013.01); A22B 5/0023 (2013.01); A22B 5/202 (2013.01); A22B 5/208 (2013.01); A22C 17/02 (2013.01); G01N 33/12 (2013.01)

(58) Field of Classification Search
    CPC ....... A22B 5/00; A22B 5/0005; A22B 5/0017; A22B 5/0023; A22B 5/20; A22B 5/201; A22B 5/202
    USPC ......................................... 452/149–157, 160
    See application file for complete search history.

(56) References Cited

U.S. PATENT DOCUMENTS 4,667,371 A  *  5/1987   Vogt    ..................... A22B 5/0023
                                                        452/152
5,162,016 A  *  11/1992  Malloy  ................ A22B 5/0029
                                                        452/149
5,334,084 A  *  8/1994   O'Brien ............... A22B 5/0005
                                                        452/134

(Continued)

Primary Examiner — Richard T Price, Jr.
(74) Attorney, Agent, or Firm — DeLio, Peterson & Curcio LLC; Peter W. Peterson

(57) ABSTRACT

A system for processing a suspended beef carcass as the carcass is moved along a defined path. A robotic arm is carried on a moveable table and has mounted thereon a servo motor-driven band saw capable of effecting a splitting operation on the beef carcass. The band saw is counterbalanced by a mass having a weight less than the weight of the band saw, and the robotic arm has a maximum load-carrying capacity less than the weight of the band saw. A torque monitor for the servo motor detects breaks in the band saw or breaks in the support for the band saw. A vision-based sensor system detects location of a tail bone on the beef carcass and identifies an age-indicating indicia. The system includes a controller in communication with the carcass rail, the carcass processing device and motor, and the vision-based sensor system.

43 Claims, 9 Drawing Sheets

(56) References Cited

U.S. PATENT DOCUMENTS

| | | | | |
|---|---|---|---|---|
| 5,820,452 A | * | 10/1998 | Jacobs | A22B 5/0005 |
| | | | | 452/117 |
| 7,404,759 B2 | * | 7/2008 | Sato | A22B 5/0041 |
| | | | | 452/157 |
| 8,070,567 B2 | | 12/2011 | Umino | |
| 8,096,860 B2 | * | 1/2012 | Bolte | A22C 17/002 |
| | | | | 452/157 |
| 8,986,081 B2 | * | 3/2015 | Ueffing | A22B 5/0041 |
| | | | | 452/156 |
| 8,992,290 B2 | * | 3/2015 | Taniguchi | A22C 17/004 |
| | | | | 452/135 |

* cited by examiner

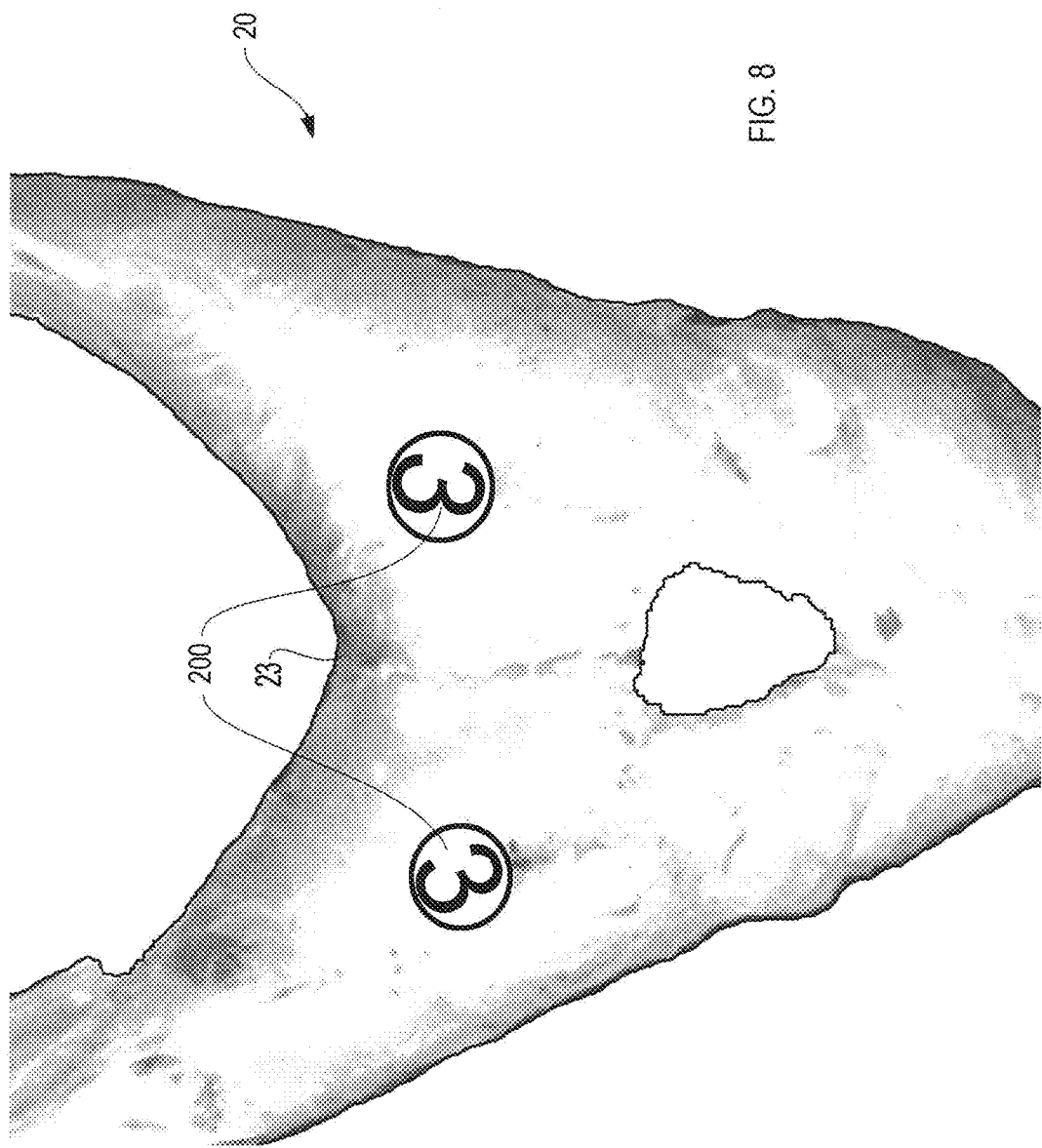

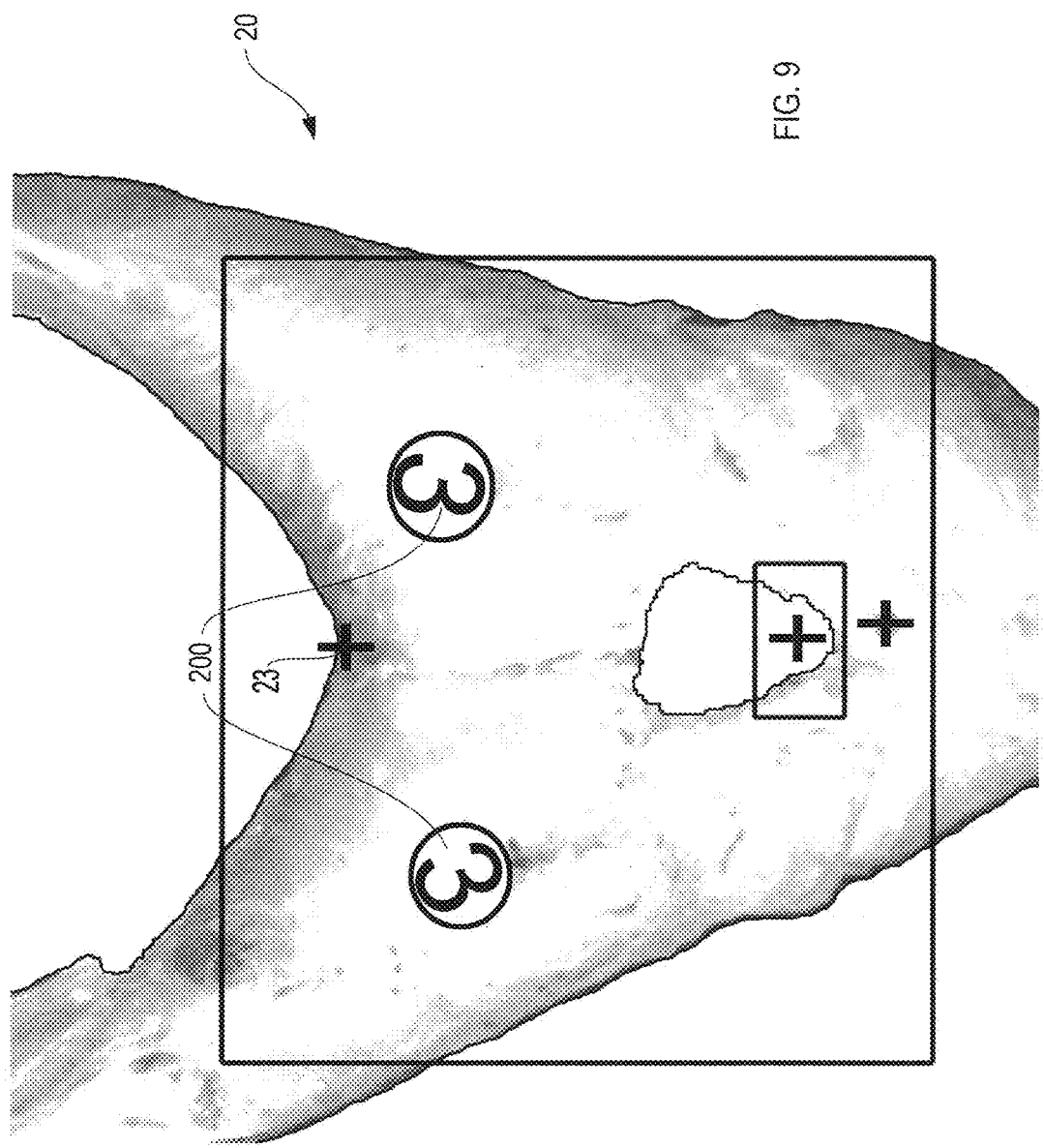

BEEF CUTTING METHOD AND SYSTEM

BACKGROUND OF THE INVENTION

1. Field of the Invention

This invention relates in general to systems and methods for splitting beef and other animal carcasses used in livestock/slaughterhouse operations.

2. Description of Related Art

Beef carcasses are cleaned and opened to remove internal components, and then split down the center of the spine or backbone into two sides, which are subsequently further processed into meat cuts. Meat processing facilities operate on beef carcasses that continuously move along an overhead carcass rail. Each carcass is suspended, typically from its hind legs, from a pair of trolleys that ride along the overhead carcass rail or track. The trolleys are driven by a chain so that each carcass moves past each processing station at a speed set by the chain. Carcasses are separated into two separate groupings identifiable by a stamp design/age-indicating indicia provided on the carcass—a first type of stamp particular to the industry denotes an animal that was over thirty months in age (hereinafter "OTM" cattle), while a second type of stamp denotes an animal that was under thirty months in age (hereinafter "UTM" cattle). Sanitizing/sterilization requirements in the industry differ when processing OTM cattle as compared to UTM cattle, thus bringing a need to properly identify each carcass and proceed with the required sanitization procedure. It is the splitting of the beef carcass down the backbone to which the systems and methods of the present invention are particularly directed.

SUMMARY OF THE INVENTION

Bearing in mind the problems and deficiencies of the prior art, it is therefore an object of the present invention to provide a beef splitting method and system whereby a robot-based carcass processing device improves the accuracy and efficiency of the carcass splitting operation.

It is another object of the present invention to provide a method and system for splitting beef carcasses that detects the tail bone location on a supported beef carcass and automatically moves the splitting saw to that location before commencing the split.

It is a further object of the present invention to provide a method and system for splitting animal carcasses using a robot-based carcass processing device with a robotic arm that has a maximum load-carrying capacity less than the weight of the splitting saw.

Another object of the present invention is to provide a method and system for splitting beef carcasses using a band saw, without the use of a support on the side of the carcass opposite the processing device.

A further object of the present invention is to provide a method and system for splitting animal carcasses that can detect breakage of the splitting saw, and control further action of the system.

Yet another object of the present invention is to provide a method and system for splitting animal carcasses that can detect breakage of the support for the carcass, and control further action of the system.

Still another object of the present invention is to provide a method and system for identifying whether an animal carcass is OTM or UTM using a vision-based sensor, and executing a sanitation procedure on a robot-based carcass processing device particular to such identification.

Still other objects and advantages of the invention will in part be obvious and will in part be apparent from the specification.

The above and other objects, which will be apparent to those skilled in the art, are achieved in the present invention which is directed to a method of processing a suspended beef carcass as the carcass is moved along a defined path. The method provides a carcass rail, a first beef carcass, a robot-based carcass processing device, a vision-based sensor system, a sanitation location, and a controller. The carcass rail has a plurality of trolleys spaced at desired intervals and is moveable along the carcass rail, each trolley capable of supporting a beef carcass. The first beef carcass is supported by the carcass trolley, and has a tail bone disposed at an upper end of the carcass, as well as indicia disposed on the carcass indicating age of the carcass. The robot-based carcass processing device has a robotic arm on which is mounted a splitting saw capable of effecting a splitting operation on a beef carcass, the robot-based carcass processing device being disposed adjacent the carcass rail. The vision-based sensor system detects age-indicating indicia on the beef carcass as the beef carcass moves on the carcass rail to a position adjacent the robot-based carcass processing device. The sanitation location executes a sanitation procedure on the splitting saw. The controller is in communication with the carcass rail, carcass processing device, and vision-based sensor system. The method includes the steps of moving the supported beef carcass on the carcass rail to a position adjacent the robot-based carcass processing device. Then, the vision-based sensor system detects the age-indicating indicia locations on the supported beef carcass as the supported beef carcass moves along the carcass rail. A signal is sent to the controller with information of the age-indicating indicia of the supported beef carcass moving along the carcass rail. The controller sends a signal to the robot-based carcass processing device to move the carcass splitting saw to the sanitation location, based on the information of the age-indicating indicia. Following a sanitation procedure on the splitting saw, the splitting saw is moved to the first or a subsequent supported beef carcass as the supported beef carcass moves along the carcass rail.

In an embodiment, a plurality of age-indicating indicia are disposed anywhere on the supported beef carcass. The method may further include executing the sanitation procedure on the splitting saw at the sanitation location prior to or after commencing the split cut, the sanitation procedure being dependent on the age-indicating indicia identified by the vision-based sensor system. The age-indicating indicia may indicate whether the beef carcass is an OTM or a UTM beef carcass. The sanitation location may be a wash cabinet. The sanitation procedure may be executed by at least one spray nozzle disposed on the splitting saw. The age-indicating indicia may comprise a stamp having a pattern thereon and the controller is capable of executing a pattern recognition procedure to identify the age of the beef carcass. The method may further include detecting locations of the tail bone and expressing the location in coordinate data in Cartesian space (X, Y, Z locations).

In another aspect, the present invention is directed to a system for processing a suspended beef carcass as the carcass is moved along a defined path, the beef carcass having at least one age-indicating indicia disposed anywhere on the carcass. The system comprises a robot-based carcass processing device, a vision-based sensor system, and a controller. The robot-based carcass processing device has a robotic arm on which is mounted a splitting saw capable of effecting a splitting operation on the beef carcass, the robot-based carcass processing device being disposed adjacent the beef carcass. The vision-based sensor is for detecting location of and identifying at least one age-indicating indicia on the beef carcass. The controller is in communication with the robot-based carcass processing device and the vision-based sensor system, the controller being capable of receiving the identified age-indicating indicia on the beef carcass from the vision-based sensor, sending a signal from the controller to the robot-based carcass processing device to execute a sanitation procedure dependent on the age-indicating indicia identified, commencing the sanitation procedure on the robot-based carcass processing device, and executing the splitting operation on the beef carcass.

In an embodiment, the system further includes a sanitation location for executing the sanitation procedure after the age-indicating indicia is identified by the vision-based sensor system. The controller may be in communication with the sanitation device. The age-indicating indicia may also indicate whether the beef carcass is an OTM or a UTM beef carcass. The sanitation location may be a wash cabinet for receiving the splitting saw, or the sanitation procedure may be executed by at least one spray nozzle disposed on the splitting saw.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

FIG. 8 is a front elevational view of a suspended beef carcass having stamps/age-indicating indicia meant for identifying the type of cattle being processed.

FIG. 9 is a front elevational view of the suspended beef carcass of FIG. 8 with the stamps/age-indicating indicia being identified in a Cartesian plane by a vision-based sensor.

DESCRIPTION OF THE EMBODIMENT(S)

In describing the embodiment(s) of the present invention, reference will be made herein to FIGS. 1-9 of the drawings in which like numerals refer to like features of the invention.

Figure 1:
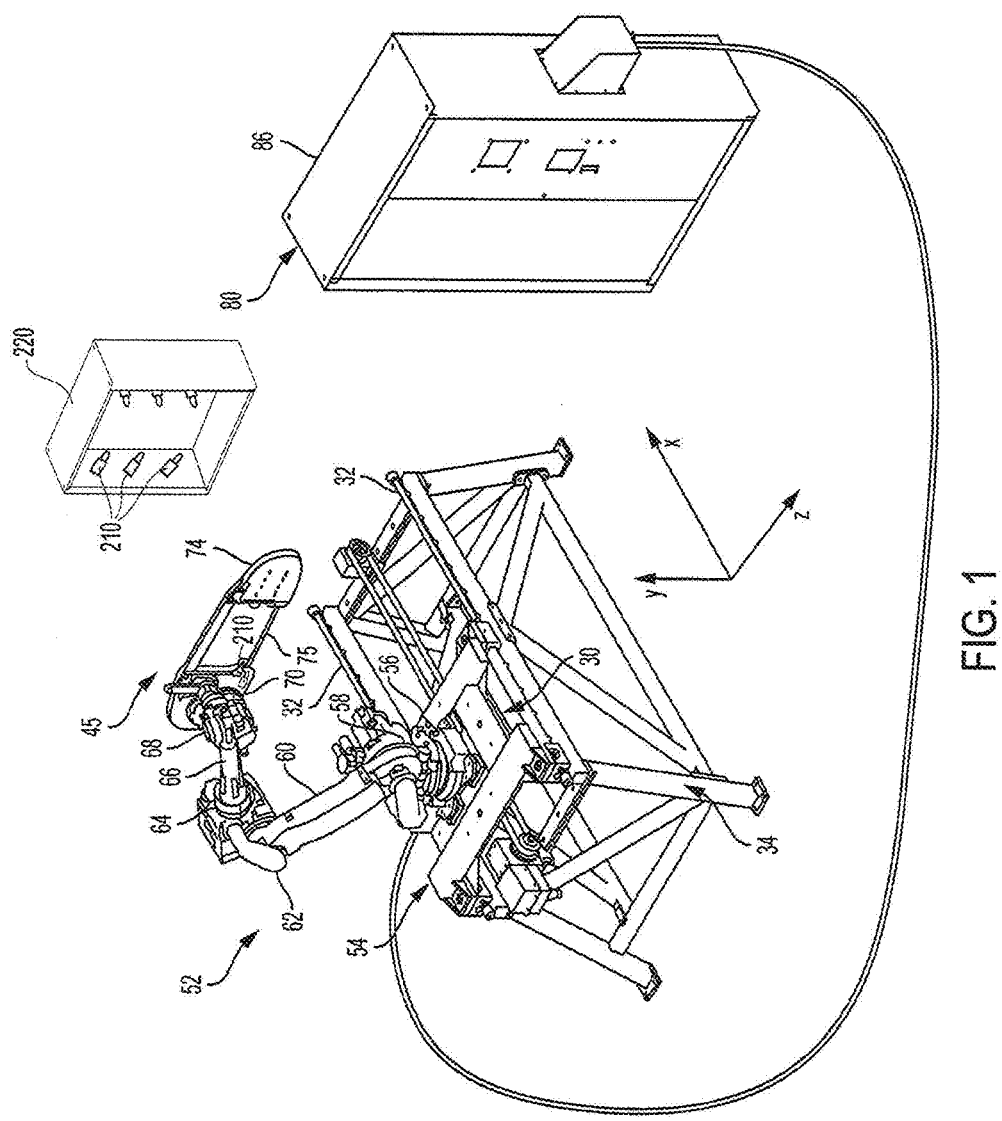
FIG. 1 is a perspective view of a processing station embodiment of the present invention in which a robot station has a band saw on a robotic arm for splitting a beef carcass.
Figure 2:
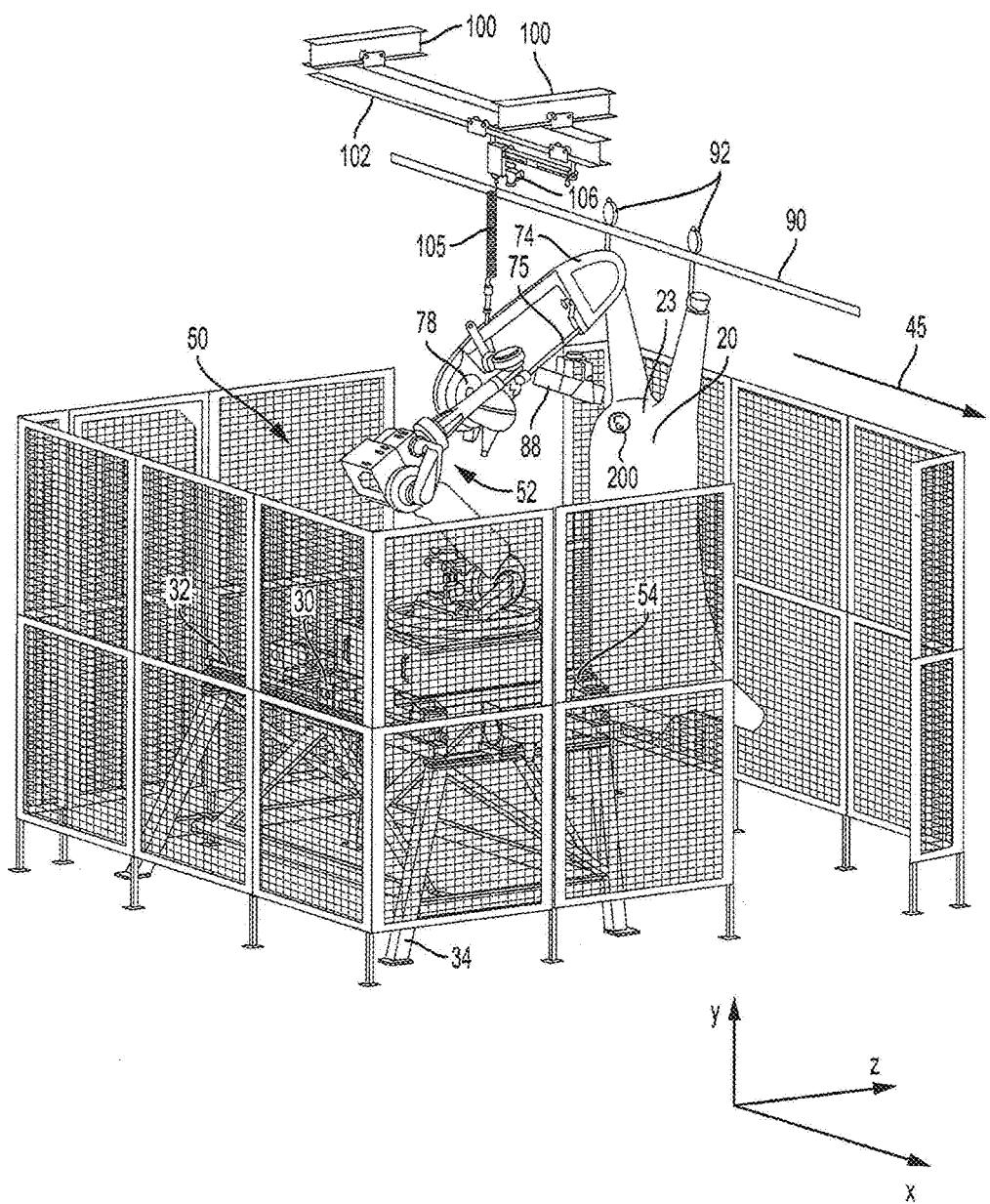
FIG. 2 is a perspective view of a processing station embodiment of FIG. 1 in which a robot station having the carcass splitting band saw on the robotic arm is supported by a saw trolley on a saw rail and positioned adjacent a carcass trolley on a carcass rail supporting the beef carcass.

Robot station 50 shown in FIGS. 1 and 2 is part of the processing station used to process the carcasses individually and sequentially as they pass by in a line suspended along carcass rail 90. An articulating robotic arm 52 is mounted on the robot station and is capable of effecting smooth and continuous movement of one or more beef processing tools or devices, such as saw arm 72, band saw 74. The robot station includes a base 54 set on four legs and mounted in a stationary position on a table 30 moveable along rails 32, which are elevated above ground level on stand 34. Rails 32 are spaced from and parallel to the path of the conveyor carrying the trolleys supporting the beef carcass (described further below). On the base is a turntable joint 56 able to swing the robotic arm 52 mounted thereon around a vertical Y-axis to various angular positions. Lower joint 58 mounted on turntable 56 is at the lower end of lower arm segment or link 60 and rotates link 60 about a horizontal axis. At the upper end of link 60 is an upper joint 62 able to rotate upper arm segment or link 66 about a horizontal L-axis. Between link 66 and the proximate end of upper joint 62 is roll joint 64 able to rotate link 66 about its longitudinal axis. A bend joint 68 at the distal end of link 66 is able to rotate saw arm 72, saw 74 about an axis normal or perpendicular to the longitudinal axis of link 66. Twist joint 70 is disposed between bend joint 68 and saw arm 72, and rotates the saw arm about an axis normal to the axis of rotation of bend joint 68. Servo or other types of electric motors are attached to and drive each of these joints.

The robotic arm 52 of the system is able to process the beef carcass while it is suspended and moving on conveyor line 90 by cutting it with the blade 75 of band saw 74 mounted on the end of the arm. The conveyor 90 is positioned adjacent the robotic arm 52 carrying the carcass-processing device, e.g., the band saw, and, optionally, a support on the opposite side of the carcass (not shown). The Cartesian coordinate space in the vicinity of the carcass and robotic arm is defined by the X-, Y- and Z-axes as shown in FIG. 1 and other drawing figures. The term "extend" or "extension" unless otherwise specified means to move generally in the Z-direction toward the conveyor and/or the carcass hanging, while the term "retract" or "retraction" unless otherwise specified means to move in the Z-direction generally away from the conveyor and/or carcass. All movement of the components described herein may be controlled by the controller 80, either on the individual processing station and trolleys, or remotely located and linked by wire or wirelessly to one or more processing stations and trolleys, and are effected using conventional actuators, drivers, motors, sensors and the like, unless otherwise specified.

Figure 3:
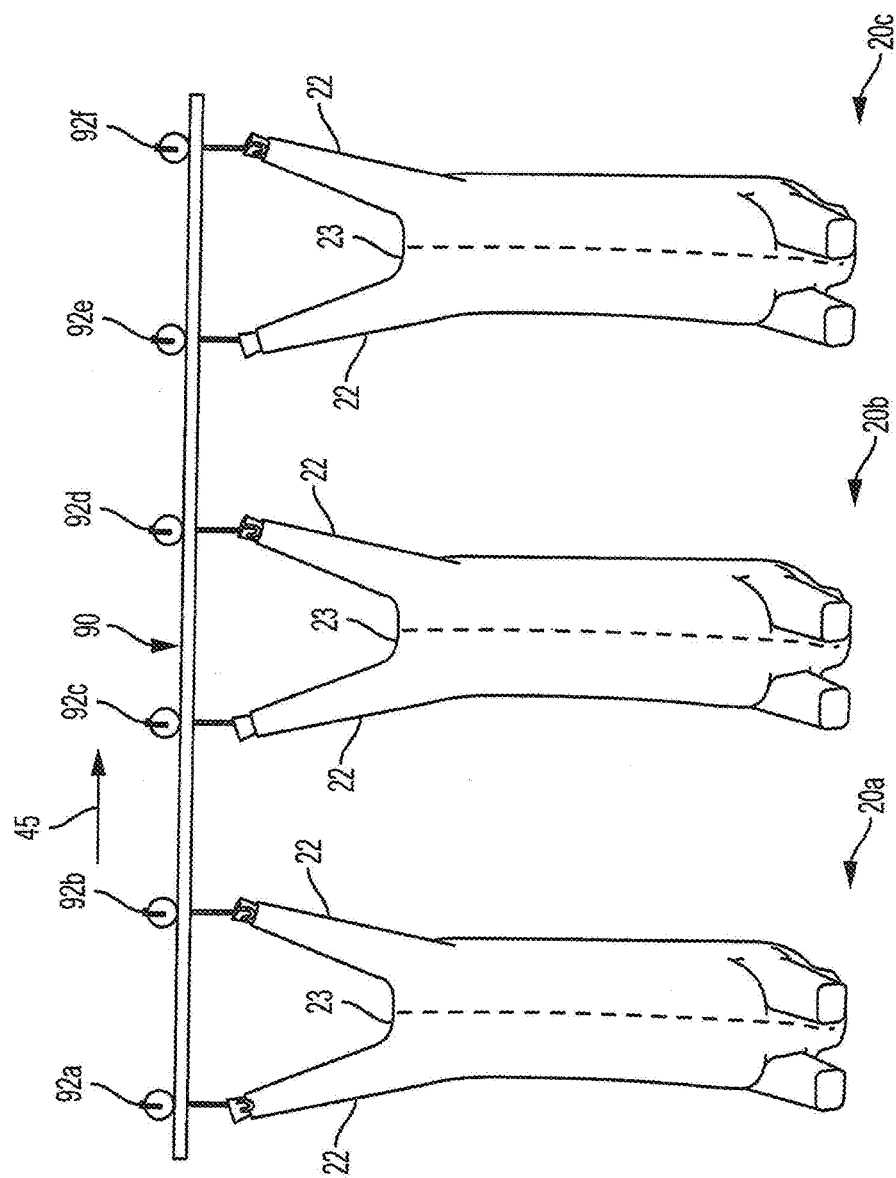
FIG. 3 is a front elevational view of a series of beef carcasses supported by trolleys on a carcass rail, to be processed by a processing station of FIG. 1.
Figure 4:
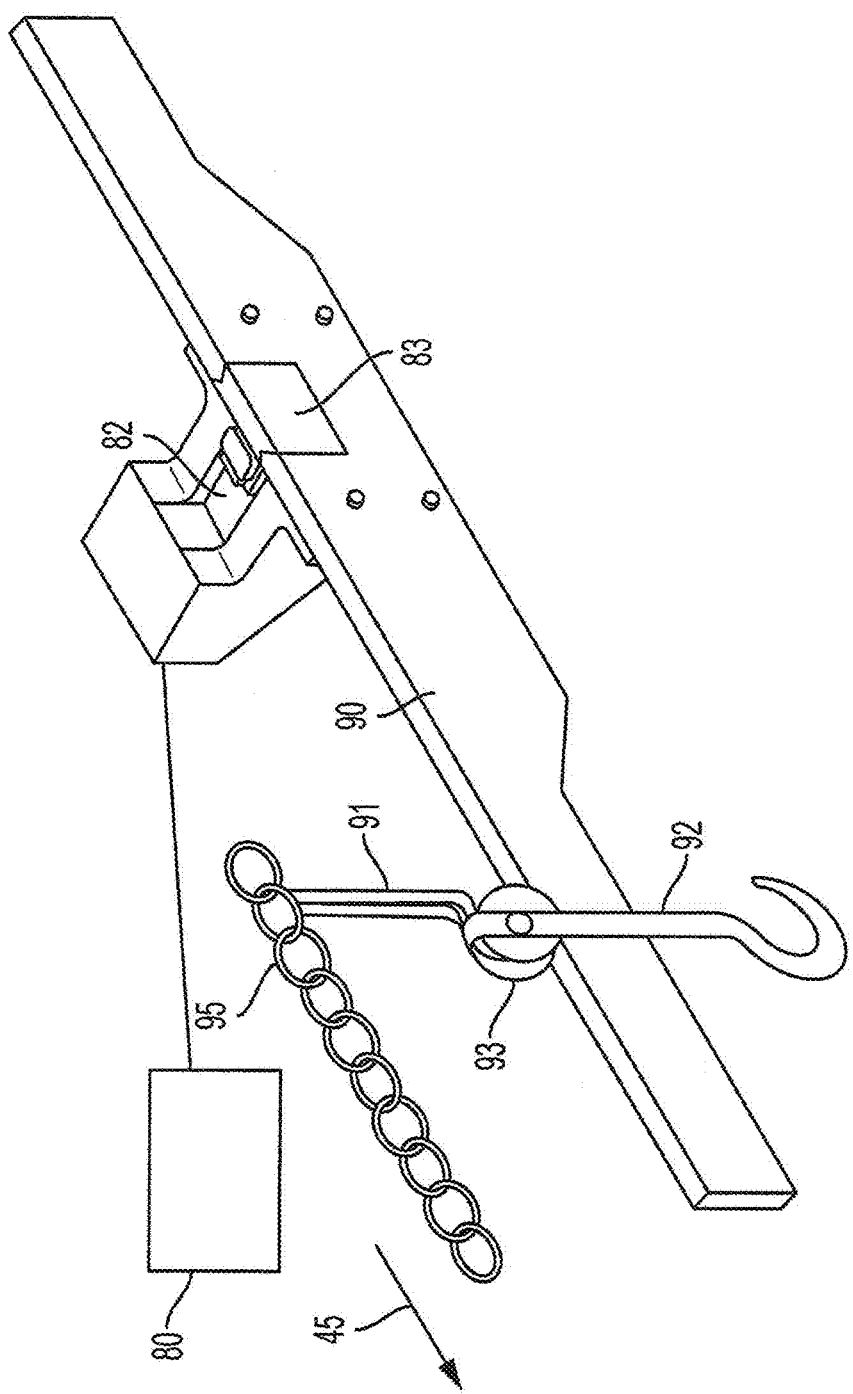
FIG. 4 is a perspective view of a portion of the carcass rail and a carcass trolley employed in connection with the processing station of FIG. 1.

The construction of an embodiment of the carcass-supporting trolley is shown in more detail in FIGS. 3 and 4, where carcass trolleys 92, 92*a, b, c, d, e, f* may ride along the upper edge of carcass rail 90. Trolleys 92 and the suspended carcass are moved along by force of a pusher member 91 which bears against the upper end of each trolley, and which is itself moved by a conveyor drive chain 95 operating at the desired speed of processing of the carcasses.

Figure 5:
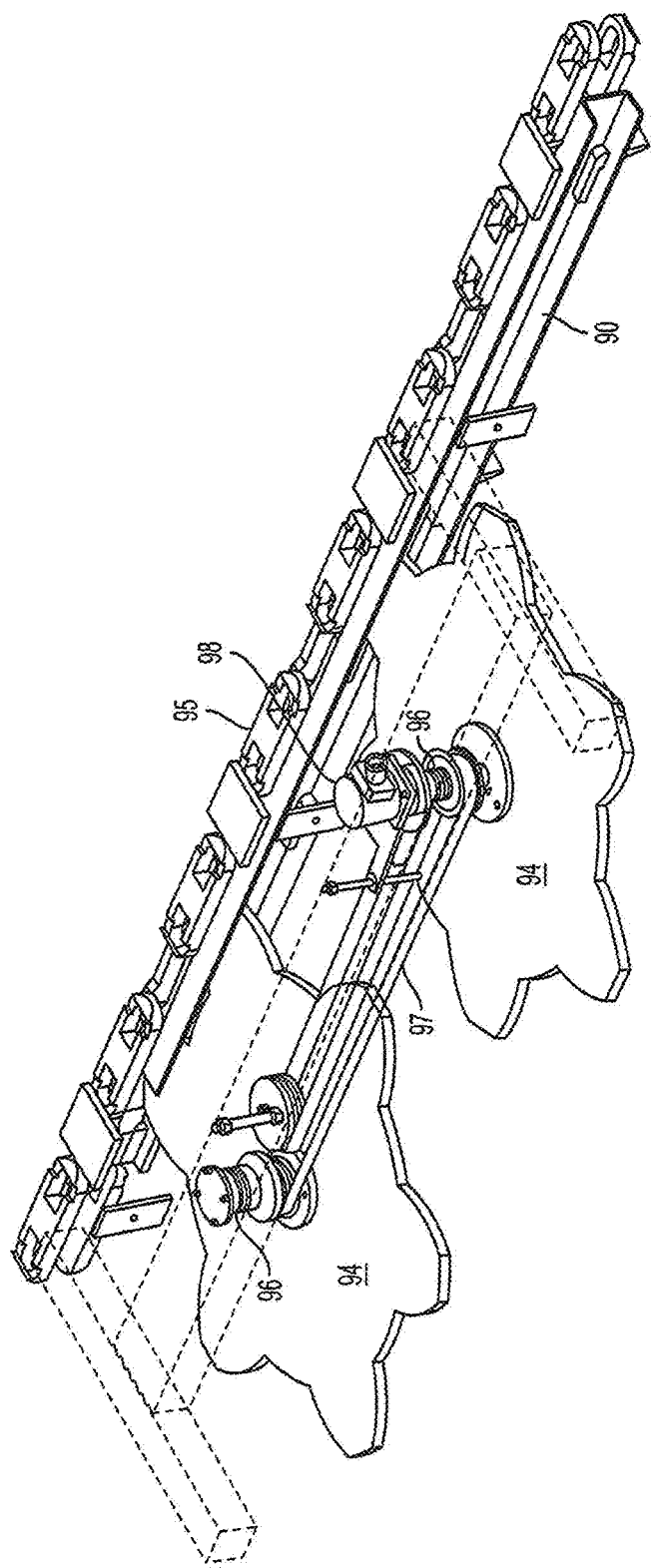
FIG. 5 is a perspective view of a chain follower mechanism for determining speed and position of a beef carcass on the carcass rail employed in connection with the processing station of FIG. 1.

Suspended beef carcasses 20, 20*a, b, c* to be split are shown hanging by hind feet 22 from hooks at the lower ends trolleys 92, 92*a, b, c, d, e, f*. The backbone or spine is shown in dotted line extending from the tail bone 23 at the base of the spine or backbone, at the upper end of the carcass. The beef carcass has a back side and a front side that is cut open (also in dotted lines) with the head and internal organs removed prior to splitting of the beef carcass. The beef carcass is supported on the carcass trolleys with the back side facing toward the robot station 50 and the front side facing away from the robot station. The X-axis location of the carcass may be tracked, for example, by a position encoder monitoring the overhead conveyor speed and position relative to the X-axis. The position encoder may be coupled to the gearbox that is driving the chain, and sends a signal corresponding to the movement of chain 95 and, correspondingly, the trolleys and carcasses. Alternatively, a chain follower mechanism as shown in FIG. 5 may be employed that engages mechanically into the side of chain 95 with plastic sprockets 94 which are attached to shafts 96. Two sprockets may be coupled together with a timing belt 97, with each sprocket having a skip tooth which allows the pusher member to pass by while the other sprocket maintains engagement into the side of the chain. The encoder 98 is attached to the sprocket shaft. The position encoder is in communication with controller 80, so that the position information of the carcass may be used by the controller to adjust the speed of the robot arm and band saw 74 on moving table 30, so that it moves alongside the carcass on the conveyor through the entire downward splitting cut.

FIG. 2 shows robot station 50 having a robotic arm assembly 52, and carcass 20 moving in direction 45 in front of the robotic arm. Robotic arm 52 also includes at its distal end a carriage having saw arm 72 which carries a band saw 74 to saw the spine in two halves vertically. In the embodiment shown, band saw 74 is also partially supported by cable 105 and a counterbalancing mechanism, which will be described further below. The plane of the saw blade 75 during cutting of the carcass is perpendicular to the direction of carcass movement 45 on carcass rail 90. Robotic arm 52 further has mounted on it a servo motor 78 that drives band saw 74. A monitor 86 is included with servo motor 78 and/or controller 80. The system of the present invention further may employ such monitor 86 as a torque monitor used for monitoring torque of the servo motor during splitting of the supported beef carcass, by monitoring the current to the servo motor driving saw blade 75. The current torque demand is monitored by a system variable that gets updated every servo interrupt, for example, at a rate of about 2000 int./sec. If there is a break in the bad saw blade during cutting through the beef carcass, there will be a significant decrease in current to the servo motor and torque output. If the algorithm for monitor 86 detects a change in torque of the servo motor during splitting of the supported beef carcass that indicates a break in the band saw during splitting of the supported beef carcass, e.g., by detecting a substantial decrease in servo motor current, controller 80 is programmed to modify operation of the robotic arm to take action to minimize and/or prevent further damage to the equipment, as will be described further below.

In the event that cable 105 breaks during cutting, more force will be applied to upper arm segment 66, supported by upper joint 62 and carrying the band saw blade. Consequently there will be a significant increase in torque on the servo motor(s) supporting and driving upper arm segment or link 66, and an increase in current to the motor(s). The system of the present invention also provides via monitor 86 the monitoring and detection of a break in a support for the splitting saw during splitting of the supported beef carcass, and modifying operation of the robotic arm. If the algorithm for the monitor 86 detects a change in torque of the servo motor driving joint 62 of supporting arm 66 during splitting of the supported beef carcass that indicates a break in the supporting cable, e.g., by detecting a substantial increase in servo motor current, controller 80 is likewise programmed to take action to minimize and/or prevent further damage to the equipment (described below).

As shown in FIG. 2, the processing station includes a pair of saw rails 100 on which ride a saw trolley 102 supporting band saw 74 by cable 105. The saw trolley moves along the saw rail in a Z-direction normal to the X-direction of the carcass trolleys 92 along conveyor 90. The band saw supported by the saw trolley is counterbalanced by mass 106 connected to the band saw by cable 105 passing through an overhead block. Counterweight mass 106 has a weight less than the weight of the band saw to permit up or down movement of the saw by a force less than the weight of the splitting saw. Mass 106 moves with band saw 74 toward and away from the beef carcass by operation of robotic arm 52. During splitting and other movement of the band saw, the load on the robotic arm does not exceed the weight of the splitting saw. The counterbalance for the band saw permits the robotic arm 52 to be designed and constructed with a lower load-carrying capacity than the weight of the band saw itself. For example, a 95 kilogram band saw may be employed on a robotic arm that has only a 50 kilogram load-carrying capacity. This permits a smaller and less costly robot station to be employed, without losing effectiveness and performance in splitting the beef carcasses. A smaller arm also allows for a much smaller footprint of the robot station.

The robotic controller 80 drives the arm and provides multiple axis interpolation for moving the carcass processing tool in Cartesian coordinate space by controlling the multiple axes of the robotic arm. The robotic controller also provides control for linear axes to drive table 30 so that the beef carcass on the carcass rail and the processing tool on the table both can be moved synchronously. The controller(s) employed in the present invention are described further below.

Figure 6:
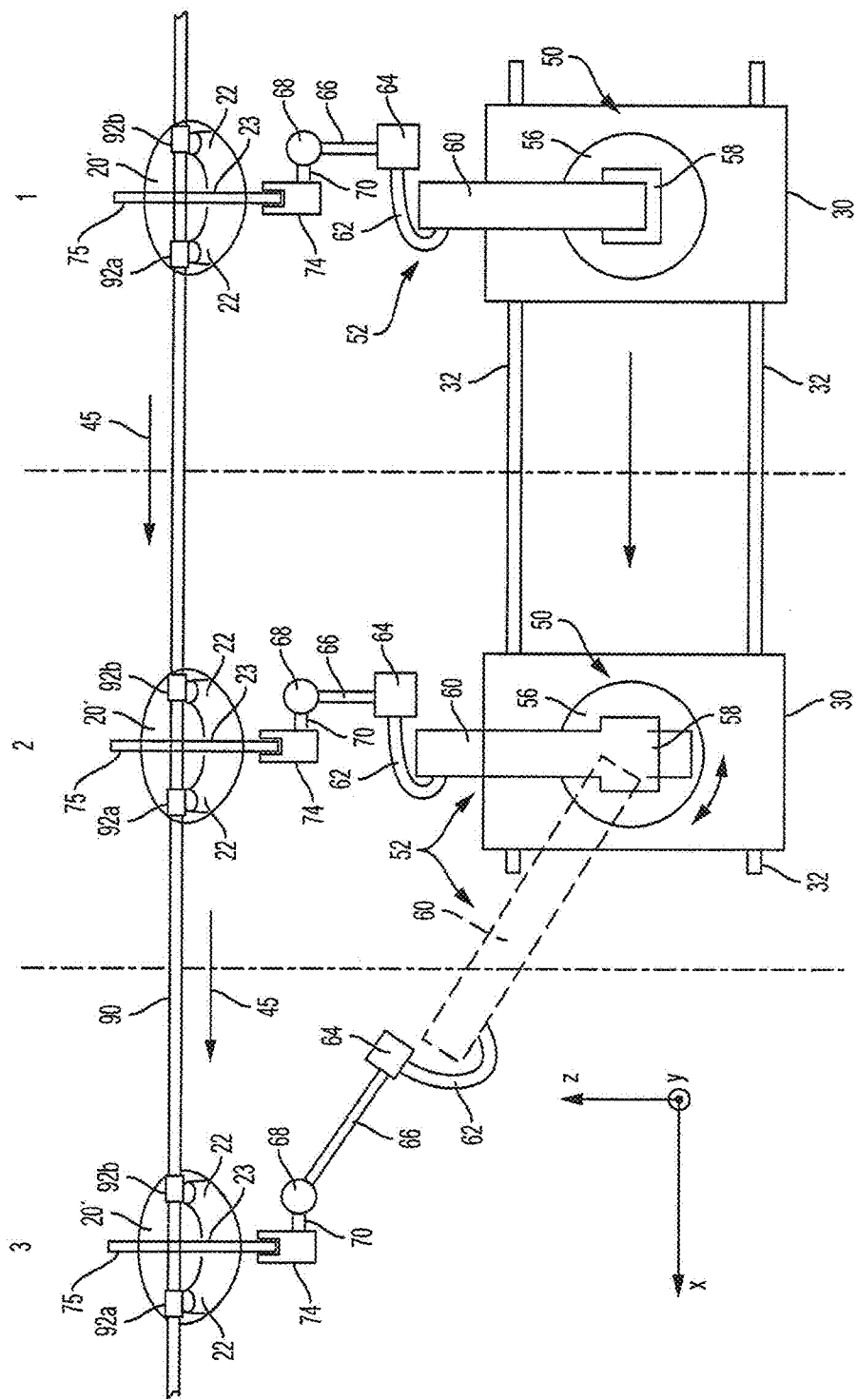
FIG. 6 is a top plan view showing the travel of a beef carcass along a carcass rail from a first position to a second position, wherein the robotic arm and saw of the processing station of FIG. 1 follow the carcass and begin to move downward to split the carcass, without the robotic arm moving horizontally relative to the base, and from the second position to a third position, wherein the base of the processing station ceases horizontal movement relative to the carcass and the robotic arm synchronously moves horizontally relative to the base along with the carcass while the robotic arm and saw continue to move downward to complete splitting of the carcass.

Table 30 supporting base 54 of robotic processing station 50 may be on a linear axis driven set of rollers on its own rails 32 as the carcass moves along the carcass rail. The drivers for table 30 are controlled by controller 80. The linear axes allow the robotic controller to move the table horizontally in the X-direction with the motion of the carcass rail. To reduce the footprint of the system of the present invention, it may employ a combination of the horizontal travel of robotic processing station 50 on the rails 32 (which axis is referred to as the U axis) and the Cartesian Xp axis movement capability of the robotic arm 52 to accomplish the total relative horizontal movement of the saw needed as the carcass moves along its rail. As shown in FIG. 6, a portion, for example, approximately half, of the travel of saw 74 may be accomplished with the U axis, wherein robotic processing station 50 moves on rails 32 with the carcass 20' from position 1, and the saw travels downward in the Y-direction only relative to base 54 on table 30 as it follows carcass 20' to position 2, and makes no horizontal X-direction movement relative to the base. The remaining portion of the horizontal travel of saw 74, for example, the other half, is accomplished by movement of saw 74 along Xp axis relative to base 54 on table 30 from position 2, while it is simultaneously continuing to move downward in the Yp direction as it follows carcass 20' to position 3. Other combinations may be used. The saw 74 will track the carcass initially with the U axis and then, when it approaches the maximum travel of that axis (position 2), table 30 motion in the X-direction will stop and movement of the saw will transition over to lateral movement with the Xp axis capability of the robotic arm 52 as link 60 (shown in phantom lines) rotates on base 56 to follow carcass 20'.

The combined synchronous vertical (Yp), horizontal (Xp) and extended/retracted (Zp) travel of the various links 60, 66, 70 and joints 56, 58, 62, 64, 68 of robotic arm 52 and saw 74 relative to the carcass as it moves continuously on the line to position 3 may be accomplished by use of a controller 80 capable of moving the carcass processing tool in Cartesian space via inverse kinematics and having interpolation control over the multiple axes of the robotic arm, as described in U.S. Patent Publication No. 2017-0049116-A1, the disclosure of which is hereby incorporated herein. Controller 80 converts the Cartesian coordinates of the tail bone location of the supported beef carcass moving along the carcass rail into coordinates usable by the robot-based carcass processing device. These latter coordinates include directional axes for the robotic arm, Xp, Yp and Zp, and rotational axes for the robotic arm Ap (roll), which revolves around the X-axis, Bp (pitch), which revolves around the Y-axis and Cp (yaw), which revolves around the Z-axis.

A dual robot may also be used on one platform, with the combined travel described herein.

As a beef carcass 20' is moved on trolleys 92, 92a, b, c, d, e, f to a positon adjacent robot station 50, controller 80 causes table 30 and the robot station base 54 on the table to commence movement alongside the carcass on carcass rail 90 as they move continuously in direction 45. In the starting position 1 (FIG. 6), saw 74 on the end of robotic arm 52 is initially located vertically near their uppermost positions and horizontally close to the point where the carcasses first enter the cutting area surrounded by the protective fencing (FIG. 2). As saw 74 begins its vertically downward cut stroke, the saw at the end of the robotic arm 52 moves horizontally on table 30 along guide track 32 in the X-direction 45 at the same speed as carcass 20' along rail 90.

During splitting of the supported beef carcass, if monitor 86 detects a change in current and torque of the servo motor that indicates a break in the band saw, controller 80 then causes the servo motor to shut down and/or robotic arm 52 to cease further downward (Y-direction) movement of the band saw through the carcass. The controller may be programmed to then simultaneously stop further movement of the beef carcasses on the trolleys 92 along the conveyor 90 and further movement of table 30 (X-direction). At that point the robotic arm may then withdraw the band saw in the Z- and/or Y-directions and extract the broken saw blade from the carcass. In the case of a change in current and torque of the servo motor that indicates a break of the supporting cable, the controller may be programmed to take the action described for the band saw break, or may be programmed to continue the downward movement of the saw through the beef carcass and complete the splitting cut, and subsequently move the saw to a safe location out of the path of the beef carcasses moving along the conveyor, disable the processing station and/or signal a fault indicator.

When the backbone has been fully split, the saw motion downward in the Y-direction has been completed. Subsequently, the robotic arm 52 with saw 74 will move away from the carcass (Z-direction) and table 30 will drive horizontally (X-direction) opposite direction 45 and the robotic arm 52 will drive saw 74 upward (Y-direction) into the starting position to engage the carcass, and the operation will be repeated.

When cutting or otherwise processing the beef carcasses, it may not be necessary to provide a support to have the carcass supported on the side opposite the carcass processing tool. It is desirable that the forces of the carcass processing tool do not move the carcass out of a known position during the processing, particularly cutting a backbone or spine. The robotic arm 52 may impart downward forces such that the supported carcass is contacted only by the band saw as it is being split, without being moved horizontally away from robotic station 50 to require a support on the opposite side. If opposing support is provided, the operation of the individual opposing support station may be the same as that described for the back station in the instant applicant's U.S. Pat. No. 6,126,536 entitled "Automated Saw for Splitting Carcasses" issued on Oct. 3, 2000 and/or published PCT application WO 2014/036547 A1 entitled "Carcass Stabilizer" published on Mar. 6, 2014, the disclosures of which are hereby incorporated by reference.

The controller of the present invention determines the position in Cartesian space of the robotic arm and tracking of the saw during the entire cut sequence, initially as the saw extends toward the carcass in the Z-direction, then as the backbone cut is made from the top of the carcass down to the bottom in the Y-direction, and finally as the saw retracts away from the carcass in the Z-direction. All saw movements occur as the saw and table follow the carcass moving in the X-direction horizontally on the carcass rail. Each robotic arm is made up of rigid segments or links connected by joints. The desired extension, end movement of the saw vertically downward along the backbone and retraction requires the computation of the dynamic change of the robotic arm joint angles to maintain the desired saw position. Successful implementation of such joint motion control also requires that the link and joint elements of the robotic arm move within their permissible physical limits. The load on the robotic arm does not exceed the weight of the splitting saw during all movement of the splitting saw. The controller may employ any known method of modeling and solving such motion problems.

The control provided by the robotic controller allows multiple axes of the robotic arm to move the processing tool in Cartesian space (X, Y, Z, A, B, C axes). The simultaneous control of movement of the table on which is mounted robotic arm 52 (on the back side of the beef carcass) ensures that they can be moved synchronously with the motion of the carcass along the rail during the entire processing operation.

As shown in the example herein, the robotic arm 52 has six (6) axes of control for the arm and a seventh axis for controlling a circular saw motor, when the invention is implemented in a carcass splitting system. The six robotic arm axes in the drawings are the rotary axes S (swing joint 56), L (lower joint 58), U (upper joint 62), R (roll joint 64), B (bend joint 68) and T (twist joint 70). The motion of these robotic arm axes are then converted into Cartesian coordinates through the motion algorithms by the processor in the controller. These Cartesian coordinates are expressed as directional axes for the robotic arm, Xp, Yp and Zp, and rotational axes for the robotic arm Ap (roll), which revolves around the X-axis), Bp (pitch), which revolves around the Y-axis and Cp (yaw), which revolves around the Z-axis.

During the sequence of carcass splitting as described above, the controller therefore employs control to move the robot joints to maintain saw 74 in a constant vertical orientation and maintaining the plane of band saw blade 75 perpendicular to the direction of carcass movement 45 as the saw extends to make contact with the carcass backbone, move downward in the Yp direction to split the backbone, retract from the carcass in the Zp direction and begin the sequence again, all while moving horizontally with the carcass and then reversing horizontal movement for the subsequent carcass. The method of splitting the beef carcass using the band saw may be completed without using a support on the opposite side of the carcass, so that the carcass supported by the trolley is contacted only by the band saw as it is being split thereby.

The present invention may also employ a vision-based sensor system utilizing a video or other camera, for example, a stereoscopic 3D camera 88 (FIG. 2) mounted above the robot station and beef carcass. The stereoscopic 3D vision system embodiment shown employs two cameras or frame grabbers that are running at 90 frames/sec, looking at the same image. One field of view of one image is at a known angle to the field of view of the other image, which allows calculation of the range data by comparison of the images, thereby allowing determination of the Cartesian location data for the carcass area of interest by the processor in the system. The vision-based sensor detects location of a tail bone 23 on the beef carcass 20 as the beef carcass moves on the carcass rail 90 to a position adjacent the robot-based carcass processing device 50. The location of the tail bone is expressed in coordinate data in Cartesian space (X, Y, Z locations). Using the processor in the vision-based sensor system, the tail bone location on the supported beef carcass may be detected in Cartesian coordinates as the supported beef carcass moves along the carcass rail. These coordinates of the tail bone location are sent by vision-based sensor system 88 in a signal to the controller, which then converts the Cartesian coordinates of the tail bone location into coordinates usable by the robot-based carcass processing device 50. These coordinates may then be used to control the directional axes for the robotic arm, Xp, Yp and Zp, and rotational axes for the robotic arm Ap (roll), Bp (pitch) and Cp (yaw). The controller may then send a signal to the robot-based carcass processing device 50 to move the blade 75 of the band saw 74 to the detected location of the tail bone 23 of the supported beef carcass as it moves along the carcass rail, to commence a splitting cut at the detected location.

The vision-based sensor system 88 may also detect an age-indicating indicia 200 in the form of a stamp having a particular design provided on each supported beef carcass 20 as the beef carcass moves on the carcass rail 90 as shown in FIGS. 2 and 8-9. Such stamps are used to indicate the age of the beef carcass 20 to be processed. Specifically, carcasses are separated into two or more separate groupings—a first type of indicia/stamp particular to the industry denotes an animal that was over thirty months in age ("OTM" cattle), while a second type of indicia denotes an animal that was under thirty months in age ("UTM" cattle). Sanitizing/sterilization requirements in the industry differ when processing OTM cattle as compared to UTM cattle. The present invention enables the system to properly identify the age-indicating indicia 200 on each carcass and initiate a sanitization procedure. While the vision-based sensor detects the location of the tail bone 23 on the beef carcass 20 as the beef carcass moves on the carcass rail 90 to a position adjacent the robot-based carcass processing device 50, it also detects the age-indicating indicia 200 provided on the carcass. The location of each age-indicating indicia 200 may vary on the carcass, and the age-indicating indicia is further processed to identify the type of stamp (and more specifically, whether the carcass is OTM or UTM) using a pattern recognition procedure (FIG. 9). Once the type of stamp is identified, the controller sends a signal to the carcass processing device 50 to execute the proper sanitation procedures (relative to whether the carcass is OTM or UTM) on its components with a sanitation device at a desired sanitation location. Such sanitation device may be accessible by the controller.

Figure 7:
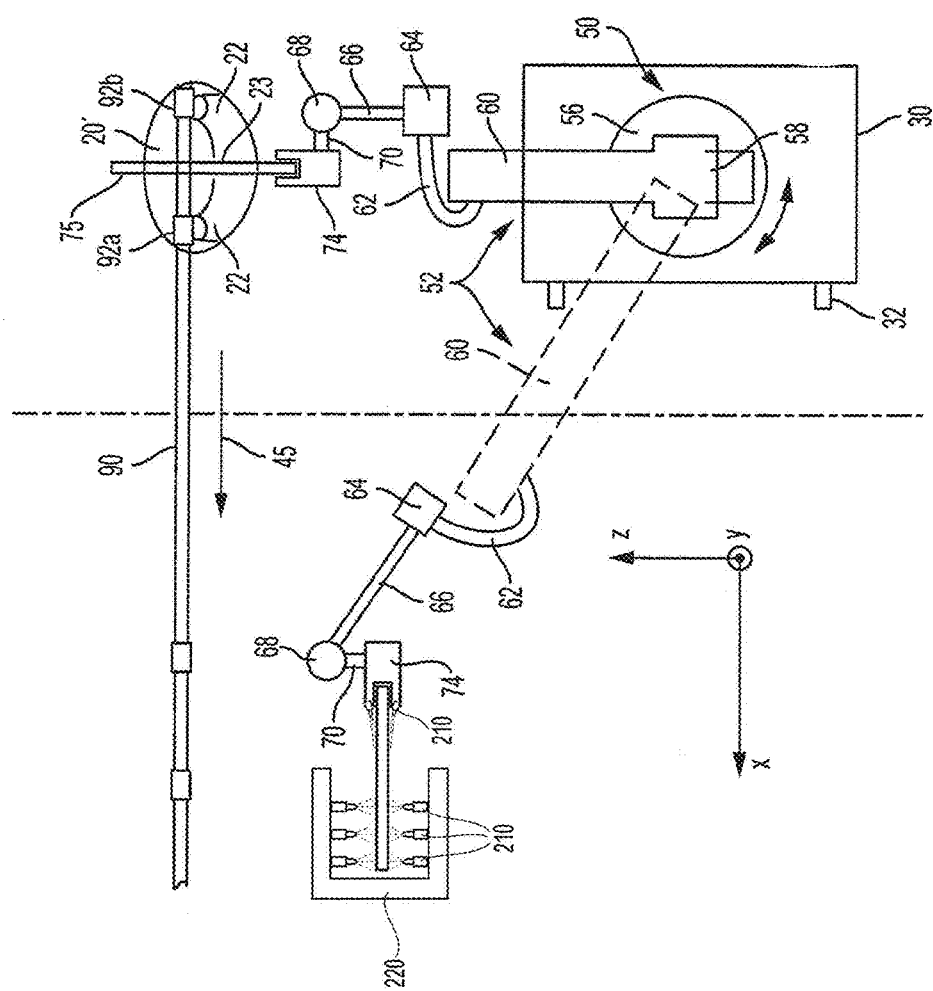
FIG. 7 is a top plan view showing the travel of a beef carcass along a carcass rail, wherein the robotic arm and saw of the processing station of FIG. 6 is inserted into a wash cabinet for sterilization prior to aligning itself with the traveling carcass to commence the splitting operation of the carcass exemplified in FIG. 6.

The sanitation procedure may be accomplished in a number of ways before and/or after the carcass having the age-indicating indicia is split. In one embodiment, sanitation is performed on the carcass processing device 50 (and more specifically, the robotic arm 52 and band saw 74) through spray nozzles 210 directly affixed on or within the band saw 74 components itself (FIGS. 1 and 7). When the vision-based sensor system 88 confirms the proper age-indicating indicia 200 on a carcass 20 (FIG. 2), arm 52 moves the saw to a desired sanitation location, such as wash cabinet 220, and the spray nozzles 210 activate, spraying the saw 74 and robotic arm 52 directly with the required sterilizing liquids (FIGS. 1 and 7).

In the alternative, wash cabinet 220 may contain all the necessary spray nozzles 210 and sterilizing liquids meant for cleaning the band saw 74 and preparing it for its next cut cycle. When the vision-based sensor 88 confirms the proper age-indicating indicia 200 on a carcass 20, the robotic arm 52 will move the band saw 74 into the wash cabinet 220, then engage the sanitation procedure while the saw 74 remains inside the cabinet until the wash cycle is complete. The carcass processing device 50 then removes the band saw 74 from the wash cabinet, now sterilized and ready to make its next cut.

Operation of the system using the robot station of the present invention may be described as follows. Table 30 supporting robotic processing station 50 is moved along rails 32 and indexed to an initial position (leftward as shown in FIGS. 1 and 2), with the robotic arm 52 supporting band saw 74 in an initial upward position. Beef carcass 20 supported by carcass trolleys 92, with its tail bone 23 disposed at an upper end of the carcass, is moved continuously on the conveyor 90 in direction 45 (rightward as shown in FIGS. 1 and 2) to a starting position adjacent the processing station 50 and saw 74. The beef carcass has its back side facing toward the processing station 50 and the front side facing away from it. Table 30 then commences movement along rails 32 synchronously with supported beef carcasses 20 while the beef carcass moves on conveyor 90. Vision-based sensor 88 detects location of tail bone 23 on beef carcass 20 as the beef carcass moves on the carcass rail, with the location being expressed in coordinate data in Cartesian space (X, Y, Z locations). Controller 80 receives the Cartesian coordinates of the tail bone location of the supported beef carcass, and converts them into coordinates usable by the robot-based processing device 50. The controller then sends a signal to the robot-based processing device 50 to move the band saw and blade 75 to the detected location of the tail bone 23 as it moves along the carcass rail. Band saw 74 then commences a split cut at the detected location of the tail bone downward through the carcass backbone, as table 30 and saw 74 are moving alongside moving beef carcass 20 on carcass rail 90. The current location of the tailbone can be tracked by a position encoder monitoring the overhead conveyor speed and position relative to the X axis plane, which position information is supplied to controller 80 causing band saw 74 to move synchronously in the X-direction with the carcass 20 moving along the conveyor. In the event that the carcass splitting is not accomplished by the time table 30 reaches the end of rails 32, table 30 stops and saw 74 continues to move horizontally by movement of arm 52 in the Xp direction relative to base 54 on robotic processing station 50, along with any extension in the Zp direction, in order to maintain synchronous movement with the moving carcass 20.

As the saw 74 is moved by the robotic arm 52, it is counterbalanced by mass 106 to permit up, down and horizontal movement of the saw using a force less than the weight of the splitting saw. During the splitting, the monitor 86 and controller 80 monitor torque of the servo motor 78 driving band saw 74. If there is a change in current to and torque of the servo motor that indicates a break in band saw blade 75 during the splitting operation, the controller causes robotic arm 52 and band saw 74 to cease downward movement and/or the movement of table 30 and supported beef carcass 20 along carcass rail 90. The robotic arm 52 then withdraws band saw 74 from the carcass. If there is a change in current and torque of the servo motor that indicates a break of the supporting cable, the same action may be taken, or alternately robotic arm 52 continues downward movement and complete the splitting cut, and subsequently moves the saw to a safe home position.

If no band saw blade breakage is detected, the cutting continues until the beef carcass is fully split. The splitting cut may be made without the use of an opposing support for the carcass, with the robotic arm 52 imparting downward forces in the Y-direction that avoids excessive force horizontally in the Z-direction so that only the band saw contacts the carcass as it is being split. Once the cut is complete, the saw motion downward is stopped, and robotic arm 52 draws saw 74 away from the carcass. Subsequently, processing station 50 with the robotic arm 52 with saw 74 on table 30 will drive horizontally opposite direction 45 (leftward as shown in FIGS. 1 and 2) to its initial position for the next carcass moving along conveyor 90. At the same time the robotic arm 52 will move saw 74 upward into the starting position to engage the carcass, and the operation will be repeated.

Alternatively, at the commencement of the splitting operation table 30 may be held in a fixed position, and the initial splitting of carcass 20 as it moves may employ horizontal movement of saw 74 by synchronized movement of robotic arm 52 in the Xp, Yp and Zp directions by the robotic processing station, using inverse kinematics with interpolation control. When the robotic arm 52 reaches its maximum degree of horizontal Xp movement, table 30 may commence movement along rails 32 synchronously with the carcass, while robotic arm 52 continues downward Yp movement of saw 74 through the carcass.

An embodiment of a robotic arm and controller of the present invention may take the form of a hardware embodiment that uses software (including firmware, resident software, micro-code, etc.). Furthermore, an embodiment may take the form of a computer program product on a tangible computer-usable storage medium having computer-usable program code embodied in the medium. A memory device or memory portion of controller 80 can form the medium. Computer program code or firmware to carry out an embodiment of the present disclosure could also reside on optical or magnetic storage media, especially while being transported or stored prior to or incident to the loading of the computer program code or firmware into the controller. This computer program code or firmware can be loaded, as an example, by connecting a computer system or external controller to the programming interface.

It should be appreciated and understood that the present invention may be embodied as systems, methods, apparatus, computer readable media, non-transitory computer readable media and/or computer program products. The present invention may take the form of an entirely hardware embodiment, an entirely software embodiment (including firmware, resident software, micro-code, etc.) or an embodiment combining software and hardware aspects that may all generally be referred to herein as a "circuit," "module" or "system." The present invention may take the form of a computer program product embodied in one or more computer readable medium(s) having computer readable program code embodied thereon.

One or more computer readable medium(s) may be utilized, alone or in combination. The computer readable medium may be a computer readable storage medium or a computer readable signal medium. A suitable computer readable storage medium may be, for example, but not limited to, an electronic, magnetic, optical, electromagnetic, infrared, or semiconductor system, apparatus, or device, or any suitable combination of the foregoing. Other examples of suitable computer readable storage medium would include, without limitation, the following: an electrical connection having one or more wires, a portable computer diskette, a hard disk, a random access memory (RAM), a read-only memory (ROM), an erasable programmable read-only memory (EPROM or flash memory), an optical fiber, a portable compact disc read-only memory (CD-ROM), an optical storage device, a magnetic storage device, or any suitable combination of the foregoing. A suitable computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computing device (such as, a computer), partly on the user's computing device, as a stand-alone software package, partly on the user's computing device and partly on a remote computing device or entirely on the remote computing device or server. In the latter scenario, the remote computing device may be connected to the user's computing device through any type of network, including a local area network (LAN) or a wide area network (WAN), or the connection may be made to an external computing device (for example, through the Internet using an Internet Service Provider).

The methods of operation of the present invention may be implemented by computer program instructions. These computer program instructions may be provided to a processor of a general purpose computing device (such as, a computer), special purpose computing device, or other programmable data processing apparatus to produce a machine, such that the instructions, which execute via the processor of the computing device or other programmable data processing apparatus, create means for implementing the functions/acts specified in the flowchart and/or block diagram block or blocks.

These computer program instructions may also be stored in a computer readable medium that can direct a computing device, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computing device, other programmable data processing apparatus, or other devices to cause a series of operational steps to be performed on the computing device, other programmable apparatus or other devices to produce a computer implemented process such that the instructions which execute on the computing device or other programmable apparatus provide processes for implementing the functions/acts specified in a flowchart and/or block diagram block or blocks.

Although the depicted embodiment of the present invention is directed to the splitting of beef carcasses, other types of carcasses may be split, and the methods described herein may be useful for splitting or otherwise processing hog and other animal carcasses.

Thus, the present invention provides a beef splitting method and system whereby a robot-based carcass processing device improves the accuracy and efficiency of the carcass splitting operation. The method and system detects the tail bone location on a supported beef carcass and automatically moves the splitting saw to that location before commencing the split. It also enables splitting of animal carcasses using a robot-based carcass processing device with a robotic arm that has a maximum load-carrying capacity less than the weight of the splitting saw. The method and system can detect breakage of the splitting saw or breakage of the support for the carcass during the splitting operation, and control further action of the system. In the case of splitting beef carcasses using a band saw, there is no need for use of a support on the side of the carcass opposite the processing device.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A method of processing a suspended beef carcass as the carcass is moved along a defined path comprising:

providing a carcass rail having a plurality of trolleys spaced at desired intervals and movable along the carcass rail, each trolley capable of supporting a beef carcass;

providing a beef carcass supported by a carcass trolley;

providing a robot-based carcass processing device having a robotic arm on which is mounted a saw capable of effecting a cutting operation on a beef carcass, robot-based carcass processing device being disposed adjacent the carcass rail;

providing a vision-based sensor system for detecting a location on the beef carcass as the beef carcass moves on the carcass rail to a position adjacent the robot-based carcass processing device, the location being expressed in coordinate data in Cartesian space (X, Y, Z locations);

providing a controller in communication with the carcass rail, the carcass processing device and the vision-based sensor system;

moving the supported beef carcass on the carcass rail to a position adjacent the robot-based carcass processing device;

using the vision-based sensor system, detecting the location on the supported beef carcass in Cartesian coordinates as the supported beef carcass moves along the carcass rail;

sending a signal to the controller with the Cartesian coordinates of the detected location of the supported beef carcass moving along the carcass rail;

converting the Cartesian coordinates of the detected location of the supported beef carcass moving along the carcass rail from the vision-based sensor system into coordinates usable by the robot-based carcass processing device;

sending a signal from the controller to the robot-based carcass processing device to move the carcass saw to the detected location of the supported beef carcass as it moves along the carcass rail;

commencing a cut at the detected location of the supported beef carcass; and moving the saw to cut the supported beef carcass as it moves along the carcass rail.

2. The method of claim 1 wherein the robot-based carcass processing device is disposed on a table, the table moving synchronously with each supported beef carcass while the beef carcass is cut.

3. The method of claim 1 wherein the saw is counterbalanced by a mass having a weight less than the weight of the saw to permit movement of the saw by the robotic arm of the robot-based carcass processing device using a force less than the weight of the saw.

4. The method of claim 1 wherein the beef carcass has a first side and a second side, the beef carcass being supported on the carcass trolley with the second side facing toward the robot-based carcass processing device and the first side facing away from the robot-based carcass processing device.

5. The method of claim 1 wherein each of the robotic arm and saw is driven by a servo motor, and further including monitoring torque of one or both of the servo motors during cutting of the supported beef carcass, detecting a change in torque that indicates a break in a blade of the saw or in a support for the saw by measuring current to the saw servo motor, and using the monitored torque to modify the cutting operation on the supported beef carcass by ceasing movement of the robotic arm of the robot-based carcass processing device and/or the movement of the supported beef carcass along the carcass rail.

6. A method of processing a suspended animal carcass as the carcass is moved along a defined path comprising:
providing a carcass rail having a plurality of carcass trolleys spaced at desired intervals and movable along the carcass rail in a first direction, each carcass trolley capable of supporting an animal carcass;
providing an animal carcass supported by a carcass trolley on the carcass rail;
providing a saw rail having a saw trolley capable of supporting a carcass saw, the saw trolley being moveable along the saw rail in a second direction normal to the first direction;
providing a carcass saw supported by the saw trolley, the saw being counterbalanced on the saw trolley by a mass having a weight less than the weight of the saw to permit movement of the saw by a force less than the weight of the saw;
providing a robot-based carcass processing device having a robotic arm attached to the saw, the robot-based carcass processing device being disposed adjacent the carcass rail, the robotic arm having a maximum load-carrying capacity less than the weight of the saw;
using the robotic arm of the robot-based carcass processing device, initially positioning the counterbalanced saw on the saw trolley at a first position away from the carcass rail;
moving the supported carcass on the carcass rail in the first direction to a position adjacent the robot-based carcass processing device;
using the robotic arm of the robot-based carcass processing device, moving the counterbalanced saw on the saw trolley along the saw rail in the second direction toward the carcass rail to a second position adjacent the supported carcass on the carcass rail;
using the robotic arm of the robot-based carcass processing device, moving the counterbalanced saw in a direction to cut the supported carcass as it moves along the carcass rail; and
using the robotic arm of the robot-based carcass processing device, moving the counterbalanced saw in the second direction away from the carcass rail to return the saw to the first position,
wherein the load on the robotic arm does not exceed the weight of the saw during all movement of the saw.

7. The method of claim 6 wherein the robot-based carcass processing device is disposed on a table, the table moving synchronously with each supported carcass while the carcass is cut.

8. The method of claim 6 wherein the saw is a band saw.

9. The method of claim 6 wherein the carcass has a first side and a second side, the carcass being supported on the carcass trolley with the second side facing toward the robot-based carcass processing device and the first side facing away from the robot-based carcass processing device.

10. The method of claim 6 wherein the carcass is a beef carcass, and further including providing a vision-based sensor system for detecting a location on the beef carcass as the beef carcass moves on the carcass rail to a position adjacent the robot-based carcass processing device, detecting the location on the supported beef carcass as the supported beef carcass moves along the carcass rail, and moving the carcass saw to the detected location of the supported beef carcass as it moves along the carcass rail to commence cutting of the supported beef carcass.

11. The method of claim 6 wherein each of the robotic arm and saw is driven by a servo motor, and further including monitoring torque of one or both of the servo motors during cutting of the supported beef carcass, detecting a change in torque that indicates a break in a blade of the saw or in a support for the saw by measuring current to the saw servo motor, and using the monitored torque to modify the cutting operation on the supported beef carcass by ceasing movement of the robotic arm of the robot-based carcass processing device and/or the movement of the supported beef carcass along the carcass rail.

12. A method of processing a suspended animal carcass as the carcass is moved along a defined path comprising:
providing a carcass rail having a plurality of carcass trolleys spaced at desired intervals and movable along the carcass rail, each carcass trolley capable of supporting an animal carcass;
providing an animal carcass supported by a carcass trolley on the carcass rail;
providing a robot-based carcass processing device having a robotic arm driven by a robotic arm servo motor on which is mounted a saw driven by a saw servo motor capable of effecting a cutting operation on a carcass, the robot-based carcass processing device being disposed adjacent the carcass rail;
providing a monitor for torque of one or both of the servo motors;
moving the supported carcass on the carcass rail to a position adjacent the robot-based carcass processing device;
using the robotic arm of the robot-based carcass processing device, moving the servo motor-driven saw toward the carcass rail to cut the supported carcass as it moves along the carcass rail;
using the monitor, monitoring torque of one or both of the servo motors during cutting of the supported carcass; and
using the monitored torque to modify the cutting operation on the supported carcass.

13. The method of claim 12 wherein the saw is a band saw.

14. The method of claim 13 further including:
using the monitor, detecting a change in torque of the band saw servo motor that indicates a break in a blade of the band saw during cutting of the supported carcass; and
ceasing movement of the robotic arm of the robot-based carcass processing device.

15. The method of claim 14 wherein the torque of the band saw servo motor is monitored by measuring current to the band saw servo motor, and change in the torque of the band saw servo motor that indicates a break in the blade of the band saw is detected by a significant decrease in current to the band saw servo motor.

16. The method of claim 14 further including ceasing movement of the supported carcass along the carcass rail.

17. The method of claim 13 wherein the robot-based carcass processing device is disposed on a table, the table moving synchronously with each supported carcasses while the carcass is cut, and further including ceasing movement of the table.

18. The method of claim 12 wherein the saw is counterbalanced by a mass having a weight less than the weight of the saw to permit movement of the saw by the robotic arm of the robot-based carcass processing device using a force less than the weight of the saw.

19. The method of claim 18 further including detecting a change in torque of the robotic arm servo motor that indicates a break in a support for the saw during cutting of the supported carcass, and modifying operation of the robotic arm.

20. The method of claim 19 wherein the torque of the robotic arm servo motor is monitored by measuring current to the robotic arm servo motor, and change in the torque of the robotic arm servo motor that indicates a break in the support for the saw is detected by a significant increase in current to the robotic arm servo motor.

21. The method of claim 12 wherein the carcass is a beef carcass, and further including providing a vision-based sensor system for detecting a location on the beef carcass as the beef carcass moves on the carcass rail to a position adjacent the robot-based carcass processing device, detecting the location on the supported beef carcass as the supported beef carcass moves along the carcass rail, and moving the band saw to the detected location of the supported beef carcass as it moves along the carcass rail to commence cutting of the supported beef carcass.

22. A method of processing a suspended carcass as the carcass is moved along a defined path comprising:
providing a line having carcasses to be processed, the line moving the carcasses horizontally past a processing station;
providing at the processing station a robot-based carcass processing device having a base and a robotic arm movable relative to the base with multiple axes of motion, the base being moveable horizontally and synchronously with a carcass moving on the line;
providing a carcass processing tool mounted to the robotic arm, the carcass processing tool comprising a saw for cutting the carcass;
providing a robotic controller in communication with robot-based carcass processing device for controlling and moving the base horizontally and in communication with the robotic arm for controlling and moving the multiple axes of the robotic arm to move the carcass processing tool in Cartesian space via inverse kinematics and having interpolation control over the multiple axes of the robotic arm;
continuously moving a plurality of carcasses on the line sequentially past the processing station;
while a selected carcass is passing the processing station, alternately: i) using the controller to synchronously move the base of the robot-based carcass processing device horizontally along with the selected carcass while the carcass processing tool saw begins to move to cut the carcass, without the robotic arm moving horizontally relative to the base, and ii) using the controller to synchronously move the robotic arm of the robot-based carcass processing device horizontally relative to the base and along with the selected carcass while the carcass processing tool saw continues to move to complete cutting of the carcass, without the base moving relative to the carcass.

23. The method of claim 22 wherein the carcass is a beef carcass and the saw is a band saw for cutting the beef carcass.

24. A system for processing a suspended beef or other animal carcass as the carcass is moved along a defined path comprising:
a carcass rail having a plurality of carcass trolleys spaced at desired intervals and movable along the carcass rail in a first direction, each carcass trolley capable of supporting a beef or other animal carcass;
a saw rail having a saw trolley capable of supporting a carcass saw, the saw trolley being moveable along the saw rail in a second direction normal to the first direction;
a carcass saw comprising a band saw driven by a servo motor and supported by the saw trolley, the band saw being counterbalanced on the saw trolley by a mass having a weight less than the weight of the band saw to permit movement of the saw by a force less than the weight of the saw;
a robot-based carcass processing device having a robotic arm attached to the servo motor and band saw, the robot-based carcass processing device being disposed adjacent the carcass rail, the robotic arm having a maximum load-carrying capacity less than the weight of the band saw;
a torque monitor for the servo motor;
a vision-based sensor for detecting a location on a beef carcass as the beef carcass moves on the carcass rail to a position adjacent the robot-based carcass processing device, the location being expressed in coordinate data in Cartesian space (X, Y, Z locations); and
a controller in communication with the carcass rail, the carcass processing device, the torque monitor and the vision-based sensor.

25. A system for processing a suspended beef carcass as the carcass is moved along a defined path comprising:
a robot-based carcass processing device having a robotic arm on which is mounted a saw capable of effecting a cutting operation on the beef carcass, the robot-based carcass processing device being disposed adjacent the beef carcass;
a vision-based sensor system for detecting a location on the beef carcass, the location being expressed in coordinate data in Cartesian space (X, Y, Z locations); and
a controller in communication with the carcass rail, the carcass processing device, and the vision-based sensor system, the controller being capable of receiving the location on the beef carcass in Cartesian coordinates from the vision-based sensor, converting the Cartesian coordinates of the location into coordinates useable by the robot-based carcass processing device, sending a signal from the controller to the robot-based carcass processing device to move the carcass saw to the detected location of the beef carcass, commencing a cut at the detected location of the supported beef carcass, and moving the saw to cut the supported beef carcass.

26. The system of claim 25 wherein the saw is a band saw.

27. The system of claim 25 wherein the saw is counterbalanced by a mass having a weight less than the weight of the saw to permit movement of the saw by the robotic arm of the robot-based carcass processing device using a force less than the weight of the saw.

28. The system of claim 25 further including a carcass rail having a plurality of carcass trolleys spaced at desired intervals and moveable along the carcass rail, each carcass trolley capable of supporting the beef carcass, and wherein:
the beef carcass has a first side and a second side;
the carcass trolley is connected to the carcass rail and is moveable along the carcass rail; and
the beef carcass is suspended on the carcass trolley, and is further supported on the carcass trolley with the second side facing toward the robot-based carcass processing device and the first side facing away from the robot-based carcass processing device.

29. The system of claim 25 wherein the saw is driven by a servo motor, and further including a torque monitor for the servo motor for monitoring torque by measuring current to the servo motor to detect a break in the saw or in support for the saw during cutting of the supported beef carcass, the controller using the monitored torque to modify the cutting operation on the supported beef carcass by ceasing movement of the robotic arm of the robot-based carcass processing device and/or movement of the supported beef carcass along the carcass rail.

30. A system for counterbalancing a saw for cutting a beef or other animal carcass comprising:
- a carcass rail having a plurality of carcass trolleys spaced at desired intervals and moveable along the carcass rail in a first direction, each carcass trolley capable of supporting an animal carcass;
- a saw rail having a saw trolley capable of supporting a carcass saw, the saw trolley being moveable along the saw rail in a second direction normal to the first direction;
- a carcass saw supported by the saw trolley, the saw being driven by a servo motor, the saw also being counterbalanced on the saw trolley by a mass having a weight less than the weight of the saw to permit movement of the saw by a force less than the weight of the saw; and
- a robot-based carcass processing device having a robotic arm attached to the saw, the robot-based carcass processing device being disposed adjacent the carcass rail, the robotic arm having a maximum load-carrying capacity less than the weight of the saw and being capable of moving the counterbalanced saw in a direction to cut the supported carcass as it moves along the carcass rail, then moving the counterbalanced saw in the second direction away from the carcass rail to return the saw to the first position.

31. The system of claim 30 wherein the saw is a band saw.

32. The system of claim 30 wherein the carcass is a beef carcass, and further including a vision-based sensor for detecting a location on the beef carcass as the beef carcass moves on the carcass rail to a position adjacent the robot-based carcass processing device, the vision-based sensor detecting the location on the supported beef carcass as the supported beef carcass moves along the carcass rail, the robotic arm moving the carcass saw to the detected location of the supported beef carcass as it moves along the carcass rail to commence cutting of the supported beef carcass.

33. The system of claim 30 wherein the saw is driven by a servo motor, and further including a torque monitor for the servo motor for monitoring torque by measuring current to the servo motor to detect a break in the saw or in support for the saw during cutting of the supported beef carcass, the controller using the monitored torque to modify the cutting operation on the supported beef carcass by ceasing of movement of the robotic arm of the robot-based carcass processing device and/or movement of the supported beef carcass along the carcass rail.

34. A system for processing a suspended animal carcass as the carcass is moved along a defined path comprising:
- a carcass rail having a plurality of carcass trolleys spaced at desired intervals and moveable along the carcass rail, each carcass trolley capable of supporting an animal carcass;
- an animal carcass supported by a carcass trolley on the carcass rail;
- a robot-based carcass processing device having a robotic arm on which is mounted a servo motor and a saw driven by the servo motor capable of effecting a cutting operation on a carcass, the robot-based carcass processing device being disposed adjacent the carcass rail; and
- a torque monitor for the servo motor capable of monitoring torque of the servo motor during cutting of the supported carcass, the torque monitor communicating the monitored torque to a controller to control operation of the servo motor during cutting of the supported carcass.

35. The system of claim 34 wherein the saw is a band saw.

36. The system of claim 34 wherein the torque monitor is capable of detecting a change in torque of the servo motor that indicates a break in the saw during cutting of the supported carcass, and communicating the change in torque to the controller; and the controller is capable of ceasing movement of the robotic arm of the robot-based carcass processing device.

37. The system of claim 36 wherein the torque monitor is capable of monitoring the torque of the servo motor by measuring current to the servo motor, and detecting change in the torque of the servo motor that indicates a break in the saw by a significant decrease in current to the servo motor.

38. The system of claim 35 wherein the robot-based carcass processing device is disposed on a table, the table moving synchronously with each supported carcass while the carcass is cut, and the controller is capable of ceasing movement of the table upon receipt of a monitored torque from the torque monitor.

39. The system of claim 34 wherein the saw is counterbalanced by a mass having a weight less than the weight of the saw to permit movement of the saw by the robotic arm of the robot-based carcass processing device using a force less than the weight of the saw.

40. The system of claim 34 wherein the torque monitor is capable of detecting a change in torque of the servo motor that indicates a break in a support for the saw during cutting of the supported carcass, and communicating this detected change to the controller, and the controller is capable of modifying operation of the robotic arm.

41. The system of claim 40 wherein the torque monitor is capable of monitoring the torque of the servo motor by measuring current to the servo motor, and detecting change in the torque of the servo motor that indicates a break in the support for the saw by a significant increase in current to the servo motor.

42. The system of claim 34 wherein the carcass is a beef carcass, and further including:
- a vision-based sensor for detecting a location on the beef carcass as the beef carcass moves on the carcass rail to a position adjacent the robot-based carcass processing device, detecting the location on the supported beef carcass as the supported beef carcass moves along the carcass rail; and
- a controller for moving the saw to the detected location of the supported beef carcass as it moves along the carcass rail to commence cutting of the supported beef carcass.

43. A system for processing a suspended carcass as the carcass is moved along a defined path comprising:
- a line having carcasses to be processed, the line moving the carcasses horizontally past a processing station;
- a robot-based carcass processing device at the processing station having a base and a robotic arm movable relative to the base with multiple axes of motion, the base being moveable horizontally and synchronously with a carcass moving on the line;
- a carcass processing tool mounted to the robotic arm; and a robotic controller in communication with robot-based carcass processing device for controlling and moving the base horizontally and in communication with the robotic arm for controlling and moving the multiple axes of the robotic arm to move the carcass processing tool in Cartesian space via inverse kinematics and having interpolation control over the multiple axes of the robotic arm, wherein the robotic controller is capable of effecting movement of the robot-based carcass processing device and the carcass processing tool to process a selected carcass, as the carcasses move continuously on the line sequentially past the processing station, alternately to: i) synchronously move the base of the robot-based carcass processing device horizontally along with the selected carcass while the carcass processing tool processes the carcass, without the robotic arm moving horizontally relative to the base, and ii) synchronously move the robotic arm of the robot-based carcass processing device horizontally relative to the base and along with the selected carcass while the carcass processes tool processes the carcass, without the base moving relative to the carcass.

* * * * *